United States Patent
Eshdat et al.

(10) Patent No.: US 8,628,965 B2
(45) Date of Patent: Jan. 14, 2014

(54) COMPOSITION OF CULTURED GRAPE CELLS

(75) Inventors: Yuval Eshdat, Rechovot (IL); Avi Perl, Rishon-lezion (IL)

(73) Assignee: The State of Israel, Ministry of Agriculture & Rural Development, Agricultural Research Organization, (A.R.O), The Volcani Center, Bet Dagan (IL)

( * ) Notice: Subject to any disclaimer, the term of this patent is extended or adjusted under 35 U.S.C. 154(b) by 0 days.

(21) Appl. No.: 13/400,173

(22) Filed: Feb. 20, 2012

(65) Prior Publication Data

US 2013/0064797 A1 Mar. 14, 2013

Related U.S. Application Data

(62) Division of application No. 11/884,774, filed as application No. PCT/IL2006/000249 on Feb. 23, 2006, now Pat. No. 8,216,801.

(60) Provisional application No. 60/655,918, filed on Feb. 25, 2005.

(51) Int. Cl.
*C12N 5/00* (2006.01)

(52) U.S. Cl.
USPC .................................. 435/430.1; 424/93.7

(58) Field of Classification Search
USPC .................. 435/430.1, 420, 29; 424/93.7
See application file for complete search history.

(56) References Cited

U.S. PATENT DOCUMENTS

| 4,714,679 A | 12/1987 | Krul |
| 6,106,872 A * | 8/2000 | Gunata et al. .................. 426/15 |
| 8,216,801 B2 * | 7/2012 | Eshdat et al. .................. 435/29 |
| 2005/0079232 A1 * | 4/2005 | Offord-Cavin et al. ........ 424/725 |

FOREIGN PATENT DOCUMENTS

| JP | 55118392 | 9/1980 |
| JP | 2529744 | 9/1996 |
| JP | 2958453 | 10/1999 |
| WO | WO 02/17945 | 3/2002 |

OTHER PUBLICATIONS

Pepin M., et al. Growth Kinetics of *Vitis vinifera* Cell Suspension Cultures. Biotechnology & Bioengineering 47(2)131-138, 1995.*

Dedaldechamp et al., Introduction of anthocyanin synthesis in nonpigmented grape cell suspensions by acting on DFR substrate availability or precursors level, Enzyme and Microbial Tech., 25 (1999), pp. 316-321.

Yamakawa et al. Formation and Identification of Anthocyanins in Cultured Cells of *Vitis* sp., Agric. Biol. Chem., 47(5), (1983), pp. 997-1001.

(Continued)

*Primary Examiner* — Ralph Gitomer
(74) *Attorney, Agent, or Firm* — Pearl Cohen Zedek Latzer Baratz, LLP

(57) ABSTRACT

A pharmaceutical or nutraceutical composition comprising a cell line callus culture of grape berry cells grown in vitro, whereby the cell line callus culture of grape berry cells is derived from one or more of grape-berry cross section, grape-berry skin, grape-berry flesh, grape seed, grape embryo of seeded or seedless cultivars or grape seed coat.

20 Claims, 8 Drawing Sheets

(56) References Cited

OTHER PUBLICATIONS

Yamakawa et al. Production of Anthocyanins by *Vitis* Cells in Suspension Culture, Agric. Biol. Chem., 47(10), (1983)—pp. 2185-2191.

Tamura et al., Production of anthocyanins form cultured cells of Muscat Bailoy, Fragrance Journal (1991)—pp. 48-53.

Hirasuna et al., Enhanced anthocyanin production in grape cell cultures, Plant Science, 78 (1991)—pp. 107-120.

* cited by examiner

COMPOSITION OF CULTURED GRAPE CELLS

CROSS-REFERENCE TO RELATED APPLICATIONS

This application is a divisional application of U.S. patent application Ser. No. 11/884,774, filed on Sep. 20, 2007, now U.S. Pat. No. 8,216,801 which is a national phase application of PCT international application no. PCT/IL2006/000249, international filing date Feb. 23, 2006, international publication no. WO 2006/090388, which in turn claims priority from U.S. provisional patent application No. 60/655,918, filed on Feb. 25, 2005, all of which are incorporated herein by reference in their entirety.

FIELD AND BACKGROUND OF THE INVENTION

The present invention relates to active health promoting ingredients from red grape cells (RGC), more particularly, to therapeutic formulations thereof.

Modern scientific thought is that chronic heart disease (CHD) and strokes are symptoms of a common illness related to a lack of cardiovascular (CV) health. Worldwide CV diseases account for half of all deaths in middle age (and considerable additional disability) and one third of all deaths in old age. Most of these deaths involve ischemic heart disease (IHD) or stroke (Lewington, 2003, Eur. Heart J. 24:1703-1704). It also incurs a substantial burden on health budgets primarily due to the high cost of hospitalization and ambulatory medical management. Although heart attacks are considered to be the major cause of death in men, recent studies have clearly shown that heart attack will strike one out of three women as well.

The process of coronary atherosclerosis development, leading to acute coronary syndromes, is comprised of four subsequent patho-physiological stages: endothelial dysfunction, plaque formation, plaque development and plaque rupture and thrombosis.

Endothelial dysfunction is the disruption of the functional integrity of the vascular endothelium as a result of exposure to cardiovascular risk factors (such as elevated LDL levels, smoking, hypertension etc.). Dysfunctional endothelium devoid of its protective properties allows the action of atherogenetic factors on the vessel wall and promotes inflammation within the wall, thus leading to increased monocyte activation, adhesion and migration, increased endothelial permeability and reduced vasodilation, thereby mediating accumulation of macrophages and lipoproteins within the wall.

Atherosclerotic plaques are formed when macrophages ingest chemically modified (usually oxidized) LDL molecules to form foam cells, which together with the T-cells and vascular smooth muscle cells (VSMC) create fatty streaks, the early form of the atherosclerotic plaque.

Inflammatory mediators and other molecules promote further development of the plaque into a fibro-fatty atheroma, which later becomes covered with a fibrous cap with a dense extracellular matrix. This cap stabilizes the plaque from rupture by making it larger.

Secretion of molecules (e.g. inflammatory molecules) by the foam cells leads to digestion of the cap matrix molecules, ultimately leading to plaque rupture, formation of a thrombus (clot) and arterial occlusion. This typically leads to a heart attack or a stroke.

Until a few years ago, most physicians considered atherosclerosis as a plumbing problem, caused by a halting of arterial blood flow by a plaque which had reached a particular size. It was claimed that the shortage of oxygenated blood to indispensable tissues, such as the cardiac muscle or brain tissue, especially at critical moments of greater need, was responsible for the induced heart or brain stroke. However, recent studies have clearly shown that in fact only about 15% of heart attacks happen this way. Pathological and other studies have demonstrated that events, which follow inflammatory processes leading to breakage of the plaque fibrous cap and resulting in blood clotting, are responsible for most heart attacks and brain strokes [Libby, 2002, Nature 420:868-874; Libby, 2004, Sci. Am. Special edition 14:50-59]. Since inflammatory processes are involved in all steps of atherogenesis, from endothelial dysfunction to plaque rupture, interference with these inflammatory mechanisms may help to prevent or fight atherosclerosis.

This new view of atherosclerosis explains the limited success and unwanted side effects of some of the medical treatments of atherosclerosis, developed during the last twenty years. For example, balloon angioplasty and stents may mediate rupturing of the residual plaques, thus eliciting strong inflammatory response. The present strategy of medically treating atherosclerosis emphasizes prevention of plaque creation and development of drugs that may cope with the processes leading to inflammation and clot formation. Such current in-use drugs include statins (inhibition of LDL biosynthesis); beta-blockers (reduce hypertension or pulse rate); aspirin (helps in prevention of inflammation or blood clotting); and anti-oxidants (prevention of LDL modification).

A strict correlation between reduction of deaths from heart diseases and increased wine consumption was reported twenty five years ago. Substantial studies clearly demonstrated the positive effect, unrelated to alcohol, of moderate red-wine consumption on coronary heart disease (CHD) mortality, known as the "French Paradox" [Renaud and de Lorgeril, 1992, Lancet 339:1523-1526; Criqui and Ringel, 1994, Lancet 344:1719-1723]. Moreover, it was suggested that polyphenols, which are present at higher concentration in red rather than white wine, act as antioxidants that protect blood low-density lipoproteins (LDL) from oxidation, a modification that is known to be a key risk factor in the development of CHD.

Recent results have demonstrated the participation of several proteins in the inflammatory processes which leads to CHD, whose levels may be regulated by constituents present in red wine: Endothelin-1 (ET-1), a potent vasoactive peptide (Kinlay et al. 2001, Curr. Opin. Lipidol. 12:383-389); endothelial nitric oxide synthase (eNOS), NO producer in endothelial cells (Leikert et al. 2002, Circulation 106:1614-1617); the platelet-derived growth factor (PDGF) which is active in VSMC (Iijima et al. 2002, Circulation 105:2404-2410) and the inflammatory marker C-reactive Protein (CRP; Aikawa & Libby, 2004, Can. J. Cardiol. 20:631-634).

Use of red wine as a source of these regulatory constituents is limited due to its high alcoholic content. Likewise, use of grapes or grape juice as a source of these active agents is limited due to their high sugar content. In addition, it has been shown that the therapeutic effect of wine and wine grapes is dependant on species, location, year (annual climate), processing etc. and therefore reliance on red wine or edible grapes as a source for consumption of these regulatory compounds does not lead to a homogeneous or consistent supply of material. Furthermore, grapes are typically contaminated by residual fungicides, pathogens, pesticides and pollutants.

A major problem associated with the potential benefit of polyphenols present in red wines and grape seed extracts lies in their bioavailability to target tissues and cells (Manach and Donovan, 2004, Free Rad. Res. 38:771-785; Williamson & Manach, 2005, Am. J. Clin. Nutr. 81:243 S-255S). Due to marked differences in their bioavailability while passing through the intestines, no obvious correlation can be drawn between the abundance of a certain polyphenol in a given food and its concentration as an active compound in vivo. The absorbance of flavonoids in the small intestines, for example, ranges from 0-60% of the dose, and elimination half-lives range from 2-48 hours [Manach and Donovan, 2004, supra]. Most polyphenols undergo extensive metabolism in the intestine, and are present in serum and urine predominantly as glucuronides, methyl or sulfate conjugates.

The mucous layer in the mouth is the potential site that provides improved absorption rates for the beneficial polyphenols. The bioavailability of trans-Resveratrol was reported to be increased if, instead of being immediately swallowed, the polyphenols were retained in the mouth for one minute before swallowing; considerable amounts of trans-Resveratrol were then measured in the plasma just two minutes after administration (Asensi et al, 2002, Free Radic Biol Med. 33:387-398). In addition, recent epidemiologic evidence supports the view that dietary flavonoids exert protective effects in oral diseases, including cancer (Browning et al, 2005, J Pharm Pharmacol. 57:1037-42) if activated by the saliva.

PCT patent application publication WO 00/35298 and PCT patent application publication WO 01/21156 teach chewing gum containing medicament active agents, including nutritional supplements such as grape seed extracts and polyphenols. Fruit cell culture preparations (e.g., extracts), or fruit cell line culture extracts are not disclosed. European patent application EP 1327441 teaches a chewing gum composition useful for reducing nicotine exposure in a subject. The agent that eliminates nicotine is an extract of a mixture of different plants, fruit and the polyphenols quercitin or catechin. Grape skin extracts are mentioned as natural pigments to color the chewing gum and not as active agents. As mentioned herein above, both grape skin and grape seed extracts provide non-defined, non-consistent and non-homogenous active agents. Unlike skin or seed extracts, fruit cell culture, and more particularly fruit cell line culture, produces highly defined phytochemicals without many of the associated interfering compounds such as sugars and pectins, in a tightly controlled environment that can be manipulated to influence the types and amounts of active compounds.

There is thus a widely recognized need for, and it would be highly advantageous to have a fruit cell, and more particularly a grape cell line extract, rich in active agents formulated to enhance bioavailability for the treatment of inflammatory disorders.

SUMMARY OF THE INVENTION

According to one aspect of the present invention there is provided a pharmaceutical composition comprising as an active ingredient a fruit cell culture and/or a preparation derived therefrom and a pharmaceutically acceptable carrier suitable for mucosal delivery.

According to another aspect of the present invention there is provided a pharmaceutical composition comprising as an active ingredient a grape cell line culture and/or a preparation derived therefrom, formulated for mucosal delivery.

According to yet another aspect of the present invention there is provided a method of treating an inflammatory disorder, the method comprising, mucosally administering to a subject in need thereof a therapeutically effective amount of a fruit cell culture having an anti-inflammatory activity and/or a preparation derived therefrom thereby treating the inflammatory disorder.

According to still another aspect of the present invention there is provided a method of treating an inflammatory disorder in a subject, the method comprising, administering to a subject in need thereof an effective amount of a grape cell line culture and/or a preparation derived therefrom, thereby treating or preventing the inflammatory disorder.

According to an additional aspect of the present invention there is provided a use of a grape cell line culture having an anti-inflammatory activity and/or a preparation derived therefrom, for treating an inflammatory disease.

According to yet an additional aspect of the present invention there is provided a use of a fruit cell culture and/or a preparation derived therefrom, for mucosally treating an inflammatory disease.

According to still an additional aspect of the present invention there is provided a method of identifying a fruit cell culture having an anti-inflammatory activity, the method comprising identifying from a plurality of fruit cell cultures, at least one culture having an anti-inflammatory activity above a predetermined threshold, thereby identifying the fruit cell culture having the anti-inflammatory activity.

According to a further aspect of the present invention there is provided a method of identifying a tasteless or tasteful fruit cell culture and/or a preparation derived therefrom, the method comprising analyzing a plurality of fruit cell cultures and/or preparations derived therefrom for taste; and selecting the tasteless or tasteful fruit cell culture and/or the preparation from the plurality of fruit cell culture, thereby identifying a tasteless or tasteful fruit cell culture and/or a preparation derived therefrom.

According to yet a further aspect of the present invention there is provided a tasteless fruit cell culture and/or a preparation derived therefrom.

According to still a further aspect of the present invention there is provided a pharmaceutical composition comprising as an active ingredient a plant cell culture and/or a preparation derived therefrom and a pharmaceutically acceptable carrier suitable for mucosal delivery.

According to further features in preferred embodiments of the invention described below, the fruit cell is a fruit cell-line.

According to still further features in the described preferred embodiments, the fruit cell comprises at least 2% polyphenols.

According to still further features in the described preferred embodiments, the fruit is selected from the group consisting of grape, apple, blueberry, prune, cranberry, elderberry, bilberry, gentain, orange, mango, kiwi, pomegranate, blackberry, raspberry, strawberry, pear, cherry, plums tomato, grapefruit, pineapple, persimmon and evodia fruit.

According to still further features in the described preferred embodiments, the grape is a colored grape.

According to still further features in the described preferred embodiments, the grape is a non-colored grape.

According to still further features in the described preferred embodiments, the fruit is of a wild variety.

According to still further features in the described preferred embodiments, the fruit is of a cultivated variety.

According to still further features in the described preferred embodiments, the mucosal delivery is selected from the group consisting of mouth delivery, pharynx delivery, esophagus delivery, rectal delivery and vaginal delivery.

According to still further features in the described preferred embodiments, the mouth delivery is selected from the group consisting of a buccal delivery and a sublingual delivery.

According to still further features in the described preferred embodiments, the preparation comprises a hydrophilic extract of said fruit cell culture.

According to still further features in the described preferred embodiments, the cell culture and/or preparation comprises at least 2% polyphenols.

According to still further features in the described preferred embodiments, the cell culture and/or preparation comprises less than 1% alcohol.

According to still further features in the described preferred embodiments, the cell culture and/or preparation is tasteless.

According to still further features in the described preferred embodiments, the cell culture and/or preparation is tasteful.

According to still further features in the described preferred embodiments, the cell culture and/or preparation is provided in a non-coloring concentration.

According to still further features in the described preferred embodiments, the cell culture and/or preparation comprises less than 10% sweetening sugar.

According to still further features in the described preferred embodiments, the cell culture or cell line culture is genetically modified.

According to still further features in the described preferred embodiments, the inflammatory disease is atherosclerosis.

According to still further features in the described preferred embodiments, the mouth delivery is affected by the group consisting of a mouthwash, a strip, a foam, a chewing gum, an oral spray, a lozenge, a capsule, a toothpaste and a food.

According to still further features in the described preferred embodiments, the mouth delivery is affected by a chewing gum.

According to still further features in the described preferred embodiments, the administering is effected mucosally.

According to still further features in the described preferred embodiments, the anti-inflammatory activity is measured by an increase in eNOS production and/or a decrease in ET-1 production in an endothelial cell culture.

The present invention successfully addresses the shortcomings of the presently known configurations by providing a fruit cell culture formulated for mucosal delivery.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
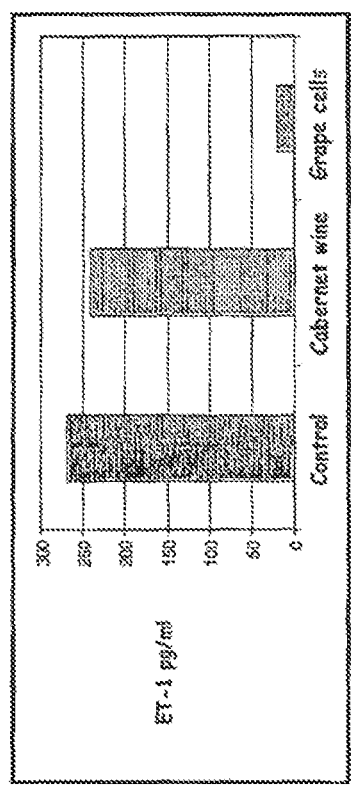
FIG. 1 is a bar graph illustrating the concentration of endothelin-1 in human endothelial cells grown on plain medium (left) and medium containing Cabernet Sauvignon wine dry-material dissolved in the medium at a concentration that is not toxic to the endothelial cells used in the bioassay (center) or red grape callus extract (right).

The present invention is of a fruit cell culture which has anti-inflammatory properties, formulated for mucosal delivery.

Specifically, the fruit cell cultures of the present invention can be used to treat inflammatory disorders such as atherosclerosis.

The principles and operation of fruit cell cultures according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Nutrapharmaceuticals derived from polyphenol-containing fruit extracts are known for their anti-inflammatory effects. However, use of fruit extracts (e.g. grape extracts) as a source of these active agents is limited due to their high sugar content. Likewise use of red wine as a source of these regulatory constituents is limited due to its high alcoholic content. In addition, it has been shown that the therapeutic effect of wine and wine grapes is dependant on species, location, year (annual climate), processing etc. and therefore reliance on red wine, grapes or grape seeds as a source of these regulatory compounds does not lend to a homogeneous or consistent supply of material. Furthermore, fruits are often contaminated by residual fungicides, pathogens, pesticides and pollutants.

In addition, the potential benefit of gastrointestinal delivery of polyphenols present in red wines and fruit extracts is limited by its bioavailability to target tissues and cells. Due to marked differences in their bioavailability while passing through the intestines, no correlation can be drawn between the abundance of a certain polyphenol in a given food and its concentration as an active compound in vivo. Absorbance of flavonoids in the small intestines, for example, ranges from 0-60% of the dose, and elimination half-lives range from 2-48 hours. Most polyphenols undergo extensive metabolism in the intestine, and are present in serum and urine predominantly as glucuronides, methyl or sulfate conjugates.

There is thus a need for novel natural (phyto) compositions which are better defined, consistent (e.g., clonal preparations), highly bioavailable and easily administered for the treatment of inflammatory disorders.

While reducing the present invention to practice, the present inventors have unexpectedly found that preparations derived from fruit (e.g., grape) cell cultures comprise more potent anti-inflammatory activities than either red wine or grape extracts. Such preparations may be formulated for mucosal delivery thereby enhancing the bioavailability of the active agents.

The present inventors have further devised a novel tool for the identification of highly potent fruit cell cultures which may be used for the treatment of inflammatory diseases.

U.S. Pat. Appl. No. 20030100082 teaches a method of isolating active agents (proanthocyanidins) from fruit cell cultures. In sharp contrast to the present invention, U.S. Pat. Appl. No. 20030100082 does not teach mucosal delivery of such agents for the treatment of inflammatory disorders. Furthermore, as opposed to the active agents described therein, the active agents of the present invention do not require extraction from fruit cell cultures. This provides a much simpler and less expensive process for the preparation of anti-inflammatory compositions.

As is illustrated hereinbelow and in the Examples section which follows, the present inventors have shown that grape cell cultures of the present invention both decrease production of the inflammatory marker ET-1 (FIG. 1) and increase the production of the anti-inflammatory marker eNOS (FIG. 2) in a human endothelial cell culture to a greater extent than both red wine and commercial grape extracts.

Thus, according to one aspect of the present invention there is provided a pharmaceutical composition including as an active ingredient a fruit cell culture and/or a preparation derived therefrom and a pharmaceutically acceptable carrier suitable for mucosal delivery.

As used herein, the phrase "pharmaceutical composition" refers to a preparation of one or more, or of a mixture, of the active ingredients described herein (i.e., fruit cell culture as further described hereinbelow) with other chemical components such as physiologically suitable carriers and excipients. The purpose of a pharmaceutical composition is to facilitate administration of a compound to an organism. Since the active ingredient is found in foods (i.e. fruit), the phrase "pharmaceutical composition" as used herein also refers to a nutraceutical composition and/or a food additive.

Herein the term "active ingredient" refers to the fruit cell culture accountable for the anti-inflammatory effect. The anti-inflammatory effect of the fruit cell culture of the present invention may be derived from an amount of active agents (e.g. polyphenols) comprised within or a particular combination or ratio of active agents comprised within the fruit cell cultures.

As used herein, the phrase "fruit cell culture" refers to a single cell fruit culture (as used herein fruit cell-line culture or clonal culture) or a heterogeneous cell culture which comprises a number of cells derived from fruits having different genotypes (e.g., different varieties) or a number of cell types or tissues derived from a single fruit. The cell cultures of the present invention may be derived from any part of the fruit e.g. fruit skin, fruit flesh, seed coat and seed flesh.

According to another aspect of the present invention, the cell culture may be derived from any part of a plant including, but not limited to endosperm, aleurone layer, embryo (or its parts as scutellum and cotyledons), pericarp, stem, leaves, tubers, trichomes and roots.

Methods of culturing fruit cells are well known in the art. For example, methods of propagating grape cells are disclosed in U.S. Pat. Nos. 4,532,733 and 6,455,312. An exemplary method of producing a grape cell line culture is described in Example 1 of the Examples section hereinbelow. Briefly, fruit explants are dissected and cultured until calli are induced. The fruit explants may be dissected in the presence of antioxidants. Examples of antioxidants and typical concentrations thereof that may be used according to this aspect of the present invention include, but are not limited to PVP (0.5 and 1 g/l), L-cysteine (150 mg/l), gallic acid (1.5 mg/l), DTT (70 mg/l), biopterin (15 mg/l), ascorbic acid (150 mg/l) and citric acid (150 mg/l). An exemplary medium which may be used to culture the fruit explants is Murashige and Skoog, MS medium (Murashige and Skoog, 1962, Physiol Plant 15:473-497), solidified with 0.25% Gelrite. The pH is typically adjusted to pH 5.9. In order to induce calli, other agents may be added to the medium such as casein hydrolisate, sucrose and inositol, Kinetin and NAA (α-naphthalenacetic acid).

Other exemplary media that may be used for calli induction of fruit cultures are listed herein below:

CP (Chee and Pool 1987, Scientia Horticulturae 32:85-95) salt and vitamins medium, also supplemented with 250 mg/l casein hydrolisate, 2% sucrose, 0.25% activated charcoal and 100 mg/l inositol (pH 5.9). For callus induction it may be supplemented with 0.2 mg/l Kinetin and 0.1 mg/l NAA (α-naphthalenacetic acid).

WPM (Woody Plant Medium), (Lloyd and McCown 1981, Int Plant Prop Soc Proc 30:421-427) salt and vitamins medium. This may be supplemented with for example, 250 mg/l casein hydrolisate, 2% sucrose, 0.25% activated charcoal and 100 mg/l inositol (pH 5.9). For callus induction it was also supplemented with 0.2 mg/l Kinetin and 0.1 mg/l NAA (α-naphthalenacetic acid).

B5 (Gamborg et al. 1968, In vitro 12:473-478) salt and vitamins medium may be supplemented with for example 250 mg/l casein hydrolisate, 2% sucrose, 0.25% activated charcoal and 100 mg/l inositol (pH 5.9). For callus induction it may be supplemented with 1 mg/l 2,4-D (2,4-dichlorophenoxyacetic acid) and 0.2 mg/l BA (6-benzyladenine).

B5 (Gamborg et al. supra) salt and vitamins medium may be supplemented with for example 250 mg/l casein hydrolisate, 6% sucrose, 0.25% activated charcoal and 100 mg/l inositol (pH 5.9). For callus induction it may be supplemented with 1 mg/l 2,4-D and 0.2 mg/l BA.

B5 (Gamborg et al. supra) salt and vitamins medium may also be supplemented with for example 1000 mg/l casein hydrolisate, 9% sucrose, 0.25% activated charcoal and 100 mg/l inositol (pH 5.9). For callus induction it may be supplemented with 2 mg/l 2,4-D, 0.5 mg/l NAA, 0.2 mg/l kinetin and 0.2 mg/l BA.

Typically, calli are visible from about ten days to four weeks following culture initiation depending on the fruit explant. Calli may be selected by color or some other physical property and subcultured for propagation in either liquid or solid cultures. In one embodiment red calli are selected from grape cultures as there is a higher content of polyphenols and anthocyanins in the red callus. Agents such as DTT (e.g. 70 mg/l), ascorbic acid (150 mg/l) or citric acid (150 mg/l) may be added to the culture medium to prevent necrogenesis. Cultures are typically subcultured every 7-10 days to fresh growing media.

As mentioned herein above, the fruit cell cultures of the present invention have anti-inflammatory activities. Selection of the appropriate fruit may be tested by numerous assays for anti inflammatory activities (e.g., as described hereinbelow and in the Examples section). Preferably, the fruit cell cultures have higher anti-inflammatory activities than either red wine or commercial grape extract in any particular assay.

Preferably, the cell cultures are derived from fruits comprising polyphenols. As used herein the term "polyphenols" refers to naturally occurring phyto organic compounds having more than one phenol group. Polyphenols may range from simple molecules such as phenolic acid to large highly polymerized compounds such as tannins. The phenolic rings of polyphenols are typically conjugated to various sugar molecules, organic acids and/or lipids. Differences in this conjugated chemical structure account for the chemical classification and variation in the modes of action and health properties of the various polyphenol compounds. Examples of polyphenols include but are not limited to, anthocyanins, bioflavonoids (including the subclasses flavones, flavonols, isoflavones, flavanols, and flavanones), proanthocyanins, xanthones, phenolic acids, stilbenes and lignans.

Preferably, the fruits comprise at least 0.1% polyphenols, more preferably at least 0.5% polyphenols, more preferably at least 1% polyphenols, more preferably at least 1.5% polyphenols, more preferably at least 2% polyphenols, more preferably at least 3% polyphenols and even more preferably 5% polyphenols. Examples of fruits that contain polyphenols include, but are not limited to grape, apple, blueberry, prune, cranberry, elderberry, bilberry, gentain, orange, mango, kiwi, pomegranate, blackberry, raspberry, strawberry, pear, cherry, plums tomato, grapefruit, pineapple, persimmon and evodia fruit.

According to a preferred embodiment of this aspect of the present invention, the fruit is a grape. The grape may be a colored grape (e.g. red, black, purple, blue and all color variations between). Alternatively, the grape may be a non-colored grape (e.g. green or white or any color variation between).

The fruit of this aspect of the present invention may be of a wild or cultivated variety. Examples of cultivated grapes include those grapes belonging to the *vitis* genus. Examples of *vitis* varieties include, but are not limited to *Vitis vinifera* (*V. vinifera*), *V. silvestris*, *V. muscadinia*, *V. rotundifolia*, *V. riparia*, *V. shuttleworthii*, *V. lubrisca*, *V. daviddi*, *V. amurensis*, *V. romanelli*, *V. aestivalis*, *V. Cynthiana*, *V. cineria*, *V. palmate*, *V. munsoniana*, *V. cordifolia*, Hybrid A23-7-71, *V. acerifolia*, *V. treleasei* and *V. betulifolia*.

Modifications to enhance the anti-inflammatory profile or the growth of the fruit cell cultures are also contemplated as being within the scope of the present invention and can be performed by one skilled in the art.

For instance, sucrose concentration may be increased in a medium (e.g. suspension medium) in order to increase the amount of pigmented polyphenols in the culture. Furthermore, nitrogen sources (e.g. $NH_4NO_3$) may be manipulated for so as to alter the polyphenol content in plant tissue cultures (Neera et al., Phytochemistry, 31(12):4143-4149, 1992). For example, decreasing the concentration of nitrogen sources in fruit cell culture medium is believed to increase the production of polyphenols in the culture. In addition, infusion of certain amino acids in the suspension medium, such as glutamine, glycine, and serine also may significantly affect the production of polyphenols in fruit cultures.

Lighting conditions can also be varied in order to achieve a modified polyphenol content in fruit culture. For example, the lighting can be changed by increasing irradiance or length of exposure to the light. Additionally, the frequency or duration of subculturing periods can be prolonged in order to improve or modify the yield of polyphenols. Other factors (e.g. growth factors) may also be added to the medium in order to enhance the growth of the fruit cultures.

The fruit cell cultures may also be genetically modified so as to express other active agents. Examples of particularly useful active agents that may be expressed include anti-inflammatory polypeptides, such as adolapin (Toxicon. 1982; 20(1):317-21), or CD4 polypeptides (see U.S. Pat. No. 5,869,055); angiogenic polypeptides (e.g. VEGF, Platelet-derived Endothelial Cell Growth Factor, Angiogenin, basic and acidic Fibroblast Growth Factor (also known as Heparin Binding Growth Factor I and II, respectively), Transforming Growth Factor-Beta, Platelet-derived Growth Factor, Hepatocyte Growth Factor, Fibroblast Growth Factor-18, prostaglandins PGE1 and PGE2, nicotinamide; and analgesic polypeptides such as Vasoactive intestinal polypeptide, and substance P.

Methods for genetically transforming plants are well known in the art. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Fruit-specific promoters such as those disclosed in U.S. Pat. No. 5,753,475 and European Pat. No. EP 973 922 A2 may be used to drive gene expression in the fruit cell cultures.

Introduction of nucleic acids by viral infection offers several advantages over other methods such as lipofection and electroporation, since higher transfection efficiency can be obtained due to the infectious nature of viruses.

As mentioned, the composition of the present invention may comprise a preparation derived from the fruit cell culture.

As used herein the term "preparation" refers to the retrieved fruit cell cultures which are used in the pharmaceutical compositions of the present invention e.g., an extract.

Preparations may be derived from fresh or frozen fruit cell cultures using any method known in the art so long as the preparations comprise the active agents. The preparation may comprise all the culture or active portions thereof (e.g., extract). The latter may be effected to increase concentration of the active ingredients or to lose undesired properties (e.g., alcohol, taste or sugar content). Thus, the fruit cell cultures may be processed by blending, grinding under liquid nitrogen and/or drying. The active agents in the fruit cell cultures may be purified prior to or following processing. Partial purification may comprise, but is not limited to disrupting fruit cellular structures thereby creating a composition comprising soluble fruit cell components, and insoluble fruit cell components which may be separated for example, but not limited to, by centrifugation, filtration or a combination thereof. Partial purification may also comprise aqueous extraction of soluble active agents by precipitation with any suitable salt, for example $KHSO_4$. Other methods may include large scale maceration and juice extraction in order to permit the direct use of the extract.

Alternatively, purification of active agents from the fruit cell culture can be effected using more sophisticated purification methods which are well known in the art including but not limited to, ultra filtration, affinity chromatography and or electrophoresis.

Testing retainment of anti-inflammatory activity can be assayed following processing as described hereinbelow.

According to a preferred embodiment of the present invention, the preparation is a dried preparation. Drying may be effected by lyophilization or placing in a heated oven e.g. at a temperature between 40° C. to 60° C. Following drying, the preparation may be further processed e.g. ground to a fine powder. The preparation may be hydrophilic or hydrophobic.

Preferably, the fruit cell cultures do not include alcohol so as to avoid alcohol associated effects such as alcoholism, liver poisoning and heart failure. In order to avoid problems associated with sugar intake, (e.g. obesity, diabetes, tooth caries), the fruit cultures of the present invention, preferably contain less than 10% w/v sweetening sugar. As used herein, the phrase "a sweetening sugar" refers to a sugar which provides a sweet taste e.g. sucrose and fructose. Preferably, the fruit cultures of the present invention comprise at least 2% w/v polyphenols. Polyphenol content may be determined using methods known in the art such as the spectrophotometric Folin-Ciocalteau test and redox derivative potentiometric titration with electrogenerated chlorine.

The fruit cell cultures or preparation of the present invention may be tasteful. However, according to a preferred aspect of the present invention, the fruit cell cultures are tasteless.

Methods of analyzing taste are well known in the art. For example, the fruit cell cultures may be subjected to an in vivo taste assay with human subjects i.e. a taste panel as described in Example 4 hereinbelow. Typically a significant number and cross-section of people blindly taste the fruit cultures of the present invention and decide accordingly on the taste. The results are statistically analyzed using parametric or non-parametric methods. In order to eliminate the influence of the difference among individual panelists and their physical conditions, in vitro and automated systems are also available to measure taste. Thus, U.S. Pat. No. 6,942,874 teaches an in vitro taste assay which may be used according to this aspect of the present invention to ascertain whether the fruit cell cultures comprise a taste. Artificial lipid membrane taste sensors are also available for performing taste recognition by measuring membrane potentials on artificial lipid membranes and polymers. Alpha M.O.S. (Toulouse, France) has developed an e-tongue which makes an analysis of the total complex chemistry of the sample (Chemical Fingerprint). The sensors have been specifically formulated to correlate to various taste attributes. Through a combination of sensor types a sensor array that is specifically focused for the pharmaceutical applications has been specified and validated. Other sensor combinations are also configurable.

As mentioned, the fruit cell cultures and/or preparations derived therefrom may be assayed for anti-inflammatory activity. Such methods are known in the art. The assays may be in-vitro or in-vivo. Examples of in-vitro anti-inflammatory assays which may be used to assess the fruit cell cultures of the present invention include inhibition of cyclooxygenase 2 activity or an increase in quinone reductase activity. Particularly preferred are the in-vitro assays which measure an increase in eNOS activity and decrease in ET-1 activity of cultured endothelial cells. Such methods are described below in Example 3.

An example of an in-vivo assay which may be used for measuring anti-inflammatory activity of the fruit cell cultures of the present invention is the Carrageenan-induced paw edema test. In this assay, paw edema is induced by injecting a volume (e.g. 100 μl or 40 μl (rats or mice, respectively) of a 1% solution of λ-carrageenan (Sigma, USA) in normal saline into the plantar surface of the left hind paw of the rats. The change in paw volumes following carrageenan administration in vehicle treated animals or animals treated with the fruit cell culture or preparation derived therefrom is measured by caliper. The anti-inflammatory activity is typically expressed as percent inhibition of paw edema.

Another example of an in-vivo assay which may be used for measuring anti-inflammatory activity of the fruit cell cultures of the present invention is the arachidonic-acid-induced inflammation of the external ear. In this assay, inflammation of the external ear is assessed by measuring tissue swelling after topical application of arachidonic acid. The acid is typically applied to the inner surface of the external ear and the opposite ear serves as control. Ear thickness may be determined using a caliper over a period of time, starting immediately following arachidonic acid application. The fruit cell cultures may be administered prior to or concomitant with arachidonic acid administration.

As mentioned herein above, in order to enhance bioavailability of the active agents present in the fruit cultures, the fruit cell cultures of the present invention together with a pharmaceutically acceptable carrier are formulated for mucosal delivery.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

As used herein the phrase "mucosal delivery" refers to the delivery of an active ingredient in which active ingredient is introduced to the body across a mucous membrane which allows for the avoidance of the gastrointestinal tract and first pass liver metabolism and consequently allows the agent to directly enter into the circulation. This can include passage through the gastrointestinal tract as by oral ingestion, but refers to delivery through the mucosa of such locus i.e. the pharynx. Examples of mucosal delivery include but are not limited to mouth delivery, pharynx delivery, esophagus delivery, rectal delivery and vaginal delivery.

It has been shown that most polyphenols undergo extensive metabolism in the intestine, and are present in serum and urine predominantly as inactive glucuronides, methyl or sulfate conjugates. The present inventors have hypothesized that mucosal delivery of the fruit cell cultures of the present invention will enhance bioavailability of active agents comprised within thereby boosting the anti-inflammatory effects.

Preferably, the site of delivery is via the mouth. Recent epidemiologic evidence supports this view since dietary flavonoids have been shown to be activated by the saliva in the mouth (Browning et al, 2005, J. Pharm. Pharmacol. 57:1037-42). Mucosal delivery via the mouth may be affected by sublingual delivery, which is systemic delivery of active agents through the mucosal membranes lining the floor of the mouth or buccal delivery, which is agent administration through the mucosal membranes lining the cheeks (buccal mucosa). Formulations which are particularly useful for mouth mucosal delivery include, but are not limited to mouthwashes, strips, foams, chewing gums, oral sprays, lozenges, foods, toothpaste and capsules. A particularly preferred formulation is a chewing gum.

The formulations, e.g. chewing gums can be low or high moisture, sugar or sugarless, wax containing or wax free, low calorie (via high base or low calorie bulking agents), and/or may contain dental agents.

The active agents of the present invention may also be encapsulated or entrapped to give a delayed release from the mucosal formulations. Any standard technique which gives partial or full encapsulation of the active agents can be used. These techniques include, but are not limited to, spray drying, spray chilling, fluid-bed coating and coacervation. These encapsulation techniques may be used individually in a single step process or in any combination in a multiple step process.

Other methods of providing delayed release formulations include, but are not limited to agglomeration to give partial encapsulation, fixation or absorption which also gives partial encapsulation, and entrapment into an extruded compound.

The amount of coating or encapsulating material on the active agent also may control the length of time for its release from chewing gum.

Generally, the higher the level of coating and the lower the amount of active agent, the slower the release. Methods and materials for formulating delayed release formulations are known in the art. Example, PCT Pat. App. publication No. WO 00/35298 teaches methods and materials for formulating delayed release formulations in chewing gums.

The active agents of the present invention (i.e. active agents derived from a particular fruit cell culture) may be formulated in different ways and administered via the same vehicle. For example, the active agents could be encapsulated for fast release, moderate release, and slow release in the same vehicle. Furthermore the active agents of the present invention may be added to a gum coating for fast release and also added to the gum center with or without encapsulation for slow release.

Faster absorption may be affected by increasing flavor levels as well as the addition of other flavor components, such as menthol and menthol derivatives, limonene, carvone, isomenthol, eucalyptol, menthone, pynene, camphor and camphor derivatives, as well as monoterpene natural products, monoterpene derivatives, and sesquaterpenes, including caryophyllene and copaene.

The formulations may include other agents which enhance the penetration of the active agents through the mucous and into the blood. Examples of such agents include, but are not limited to 23-lauryl ether, Aprotinin, Azone, Benzalkonium chloride, Cetylpyridinium chloride, Cetyltrimethylammonium bromide, Cyclodextrin, Dextran sulfate, Lauric acid, Lauric acid/Propylene glycol, Lysophosphatidylcholine, Menthol, Methoxysalicylate, Methyloleate, Oleic acid, Phosphatidylcholine, Polyoxyethylene, Polysorbate 80, Sodium EDTA, Sodium glycocholate, Sodium glycodeoxycholate, Sodium lauryl sulfate, Sodium salicylate, Sodium taurocholate, Sodium taurodeoxycholate, Sulfoxides and various alkyl glycosides.

Other modifications may also affect the release rate of the active agents into the mucosa. Texture modifiers to soften base may give faster release where hard bases may give slower release. Addition of alkaline materials such as sodium bicarbonate or sodium hydroxide may make the saliva slightly alkaline, which may increase buccal/lingual absorption of the medicament into the bloodstream.

Release of the active agents of the present invention may also be affected by the shape and size of the formulation. For example, flat stick pieces of gum with large surface area may release actives faster into saliva from gum when chewed, whereas round or cube pieces may release medicaments and actives more slowly.

Tableting of chewing gum is disclosed in U.K. Patent Publication No. 1,489,832; U.S. Pat. No. 4,753,805; EP Patent Publication No. 0 221 850; and Italy Patent Publication No. 1,273,487. These patents disclose active agents added to chewing gum which is then tableted.

Coloring agents may also be added to the formulations. Coloring agents contemplated by the present invention include food quality dyes. Film formers preferably added to the syrup include methyl cellulose, gelatins, hydroxypropyl cellulose, ethyl cellulose, hydroxyethyl cellulose, carboxymethyl cellulose and the like and combinations thereof. According to a preferred embodiment, fruit cell cultures of the present invention are provided in a non-coloring concentration.

As mentioned above, the fruit cell cultures of the present invention may be tasteful and agents which offset a bitter taste may be added e.g. sodium salts. In addition, sweeteners may be added. The sweeteners may comprise sugarless or sugar-containing components.

For administration by nasal inhalation, the active ingredients for use according to the present invention may be conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparation of the present invention may also be formulated in rectal compositions such as suppositories or retention enemas, using, e.g., conventional suppository bases such as cocoa butter or other glycerides.

As mentioned hereinabove, the fruit cell cultures of the present invention and preparations derived therefrom may also be provided as food additives and ingested orally.

The phrase "food additive" [defined by the FDA in 21 C.F.R. 170.3(e)(1)] includes any liquid or solid material intended to be added to a food product. This material can, for example, include an agent having a distinct taste and/or flavor or a physiological effect (e.g., vitamins). In addition the fruit cell cultures and preparations derived therefrom may be provided to animals as feed additives.

The food additive composition of the present invention can be added to a variety of food products. Preferably, the fruit cell cultures of the present invention are added to foods which are retained in the mouth prior to swallowing so as to enhance mucosal delivery. Examples of such foods include chocolates, sweets and ice-creams.

As used herein, the phrase "food product" describes a material consisting essentially of protein, carbohydrate and/or fat, which is used in the body of an organism to sustain growth, repair and vital processes and to furnish energy. Food products may also contain supplementary substances such as minerals, vitamins and condiments. See Merriani-Webster's Colliegate Dictionary, 10th Edition, 1993. The phrase "food product" as used herein further includes a beverage adapted for human or animal consumption.

A food product containing the food additive of the present invention can also include additional additives such as, for example, antioxidants, sweeteners, flavorings, colors, preservatives, nutritive additives such as vitamins and minerals, amino acids (i.e. essential amino acids), emulsifiers, pH control agents such as acidulants, hydrocolloids, antifoams and release agents, flour improving or strengthening agents, raising or leavening agents, gases and chelating agents, the utility and effects of which are well-known in the art.

According to another aspect of the present invention, grape cell line cultures and preparations derived therefrom may be formulated for other modes of delivery including oral, intestinal or parenteral delivery, including intramuscular, subcutaneous and intramedullary injections as well as intrathecal, direct intraventricular, intravenous, inrtaperitoneal, intranasal, or intraocular injections.

For injection, the active ingredients of the pharmaceutical composition may be formulated in aqueous solutions, preferably in physiologically compatible buffers such as Hank's solution, Ringer's solution, or physiological salt buffer.

Thus the grape cell cultures and preparations derived therefrom described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active compound in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the conjugates to allow for the preparation of highly concentrated solutions.

Pharmaceutical compositions suitable for use in context of the present invention include compositions wherein the active ingredients are contained in an amount effective to achieve the intended purpose. More specifically, a therapeutically effective amount means an amount of active ingredients (fruit cell culture) effective to prevent, alleviate or ameliorate symptoms of a disorder (e.g., atherosclerosis) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays such as the ET-1 and eNOS cell culture assays described in Example 3 hereinbelow. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Since the fruit cell cultures of the present invention comprise anti-inflammatory activities, they may be used for treating a disease which is associated with inflammation.

Thus, according to another aspect of the present invention there is provided a method of treating an inflammatory disorder, comprising mucosally administering to a subject in need thereof a therapeutically effective amount of a fruit cell culture and/or a preparation derived therefrom thereby treating the inflammatory disorder.

As used herein the term "treating" refers to the prevention of some or all of the symptoms associated with an inflammatory disease, a condition or disorder. The term "treating" also refers to alleviating the symptoms or underlying cause of an inflammatory disease, prolongation of life expectancy of patients having a disease, as well as complete recovery from a disease.

As used herein the phrase "inflammatory disorder" includes but is not limited to chronic inflammatory diseases and disorders and acute inflammatory diseases and disorders. Examples of such diseases and conditions are summarized infra.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2): 49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8): 1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49;77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med. Sci. 2000 April; 319 (4):234), myasthenic diseases, Lambert-Eaton myasthenic syndrome (Takamori M. Am J Med. Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad. Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J. Cardiol. 1999 Jun. 17; 83 (12A):75H), thrombocytopenic purpura (Moccia F. Ann Ital Med. Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci U S A 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3): 139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J. Cardiol. 1999 Jun. 17; 83 (12A):75H), thrombocytopenic purpura (Moccia F. Ann Ital Med. Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med. Sci. 2000 April; 319 (4):234), myasthenia, Lambert-Eaton myasthenic syndrome (Takamori M. Am J Med. Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad. Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

According to a preferred embodiment of this aspect of the present invention, the disorder is atherosclerosis or an inflammatory disease of the mouth or gums.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of Red Grape Cell Lines

Materials and Methods

Plant Material:

Plant material was extracted from calli derived from all parts of grape cross sections, grape skin cells and grape seed coats.

Calli from Grape Cross Sections:

Young grape bunches, 4 to 8 cm long, were harvested from field grown grape plants 20-50 days post anthesis and were thoroughly rinsed in running tap water. Green immature berries of the seedless grape *Vitis vinifera* cv. "AVNIR 825" (a cross between Agraman and Gamay red) were sterilized for 10 minutes in a solution containing 1.3% w/v sodium hypochlorite and (0.1% v/v) Tween 20, as a wetting agent. Explants were dissected, using a scalpel, into 2 to 3 mm long traversal sections under half-strength MS (Murashige and Skoog, 1962, Physiol Plant 15:473-497) liquid basal medium supplemented with filter-sterilized 1.7 mM ascorbic acid and 0.8 mM citric acid, 100 mg/l DTT (dithiothreitol) and 50 mg/l acetyl cysteine. The following antioxidants were added to the cutting medium: PVP (0.5 and 1 g/l), L-cysteine (150 mg/l), gallic acid (1.5 mg/l), DTT (70 mg/l), biopterin (15 mg/l), ascorbic acid (150 mg/l) and citric acid (150 mg/l) in order to inhibit cell necrogenesis and to enable the recovery of green, health berry disks.

Berry disks were placed in 100×15 mm culture plates containing 25 ml of autoclaved Murashige and Skoog, MS medium, solidified with 0.25% Gelrite. The pH was adjusted to pH 5.9 prior to autoclaving at 102 kpa for 15 minutes. Thirty plates each containing 25 berry disks, were sealed with Parafilm and incubated in the dark at 26° C. for three days. Cultures were incubated at 25° C. under a 16-h photoperiod of 15-30 $\mu molm^{-2}s^{-1}$ irradiance provided by cool-white fluorescent tubes. MS salt and vitamins medium was also supplemented with 250 mg/l casein hydrolisate, 2% sucrose and 100 mg/l inositol. For callus induction it was also supplemented with 0.2 mg/l Kinetin and 0.1 mg/l NAA (α-naphthalenacetic acid) media designated as RD1.

3-4 weeks following culture initiation, a mixture of green and red callus was visible along the berry disks. The callus was composed of friable, elongated cells, some of which exhibited a dark pigmentation of anthocyanins. Callus sector enriched in anthocyanins were selected and individually subcultured for propagation. Green callus sectors were cultured separately.

Calli from Grape Skin Cells:

Young grape bunches, 4 to 8 cm long, were harvested 20-50 days post anthesis from field grown grape plants and were thoroughly rinsed in running tap water. Green immature berries of the seedless grape *Vitis vinifera* cv. "AVNIR 825" (a cross between Agraman and Gamay red) were sterilized for 10 minutes in a solution containing 1.3% w/v sodium hypochlorite and (0.1% v/v) Tween 20, as a wetting agent. Berry skins were isolated by producing a cut of 3-8 mm in the berry skin and peeling off only the skins using a sterile forceps. Skin isolation was performed under half-strength MS (Murashige and Skoog, 1962) liquid basal medium supplemented with filter-sterilized 1.7 mM ascorbic acid and 0.8 mM citric acid, 100 mg/l DTT (dithiothreitol) and 50 mg/l acetyl cysteine.

Berry skins were placed in RD-1 culture media. Following about 10-14 days, cell clumps started to develop on the cut surface of the skin pills. Cell, enriched in anthocyanins, were selected and further subcultured into fresh media for further propagation.

Calli from Grape Seed Coats:

Young grape bunches, 4 to 8 cm long, were harvested 20-50 days post anthesis from field grown grape plants and were thoroughly rinsed in running tap water. Green immature berries of the seedless grape *Vitis vinifera* cv. "AVNIR 825" were sterilized for 10 minutes in a solution containing 1.3% w/v sodium hypochlorite and (0.1% v/v) Tween 20, as a wetting agent. Berries were cut open to reveal the young green developing seeds. Immature seed coats were dissected and placed on culture medium. Isolation was performed under half-strength MS (Murashige and Skoog, 1962) liquid basal medium supplemented with filter-sterilized 1.7 mM ascorbic acid and 0.8 mM citric acid, 100 mg/l DTT (dithiothreitol) and 50 mg/l acetyl cysteine.

The seed coat sections were placed in RD-1 culture media. After about 12-20 days, seed coats turned brown and a callus started to appear on top of the seed coat explants. Cell, enriched in red-brown pigmentation, were selected and further subcultured into fresh media for further propagation.

Establishment of Liquid Cultures:

Liquid cultures were established by addition of 10 g of callus into 50 ml of the different media (RD1-RD6-see below). All cell lines that were successfully established on solid media developed a homogenous cell suspension in the same media combinations but lacking a gelling agent. The addition of 70 mg/l DTT or 150 mg/l of either ascorbic acid or citric acid improved growth and inhibited cell necrogenesis of berry derived suspension culture. All explant types were successfully utilized for the establishment of liquid cultures. Cultures were routinely subcultured every 7-10 days to fresh growing media.

Additional *Vitis* Species that were Introduced in Order to Establish Berry Derived Callus Cell Lines:

The following *Vitis* species were cultured using the above mentioned protocol:

*Vitis silvestris, V. muscadinia, V. rotundifolia, V. riparia, V. shuttleworthii, V. lubrisca, V. daviddi, V. amurensis, V. romanelli, V. aestivalis, V. Cynthiana, V. cineria, V. palmate, V. munsoniana, V. cordifolia,* Hybrid A23-7-71, *V. acerifolia, V. treleasei, V. betulifolia.*

Additional Media Utilized for the Establishment of Calli from the Different *Vitis* species:

CP (Chee and Pool 1987, Scientia Horticulturae 32:85-95) salt and vitamins medium, also supplemented with 250 mg/l casein hydrolisate, 2% sucrose, 0.25% activated charcoal and 100 mg/l inositol (pH 5.9). For callus induction it was also supplemented with 0.2 mg/l Kinetin and 0.1 mg/l NAA (α-naphthalenacetic acid), media designated as RD2.

WPM (Woody Plant Medium), (Lloyd and McCown 1981, Int Plant Prop Soc Proc 30:421-427) salt and vitamins medium was also supplemented with 250 mg/l casein hydrolisate, 2% sucrose, 0.25% activated charcoal and 100 mg/l inositol (pH 5.9). For callus induction it was also supplemented with 0.2 mg/l Kinetin and 0.1 mg/l NAA (α-naphthalenacetic acid), media designated as RD3.

B5 (Gamborg et al. 1968, In vitro 12:473-478) salt and vitamins medium was also supplemented with 250 mg/l casein hydrolisate, 2% sucrose, 0.25% activated charcoal and 100 mg/l inositol (pH 5.9). For callus induction it was also supplemented with 1 mg/l 2,4-D (2,4-dichlorophenoxyacetic acid) and 0.2 mg/l BA (6-benzyladenine), media designated as RD4.

B5 (Gamborg et al. supra) salt and vitamins medium was also supplemented with 250 mg/l casein hydrolisate, 6% sucrose, 0.25% activated charcoal and 100 mg/l inositol (pH 5.9). For callus induction it was also supplemented with 1 mg/l 2,4-D and 0.2 mg/l BA, media designated as RD5.

B5 (Gamborg et al. supra) salt and vitamins medium was also supplemented with 1000 mg/l casein hydrolisate, 9% sucrose, 0.25% activated charcoal and 100 mg/l inositol (pH 5.9). For callus induction it was also supplemented with 2 mg/l 2,4-D, 0.5 mg/l NAA, 0.2 mg/l kinetin and 0.2 mg/l BA, media designated as RD6.

Results

The efficiency of callus production of *Vitis vinifera* grape cross sections, grape skins and grape seeds is exemplified in Table 1 hereinbelow.

TABLE 1

| Explant type | Number of plate cultured | % of plated producing calli | Type of callus produced |
|---|---|---|---|
| Berry disks | 537 | 64 | Light red to purple |
| Skin | 498 | 51 | Dark red to purple |
| Seed coat | 428 | 49 | Red brownish |

The efficiency of production of the different callus 'types' from some of the *Vitis* species utilized in this study is summarized in Table 2 hereinbelow.

TABLE 2

| Vitis species | Explant type | Average efficiency of callus production (%) | Callus type | Optimal Media |
|---|---|---|---|---|
| *Muscadinia (rutondifolia)* | B SC, S | 43 | Dark red | RD1 |
| *shuttleworthii* | B SC, S | 29 | Red | RD3 |
| *aestivalis* | B SC, S | 36 | Dark red | RD2 |
| Hybrid A23-7-71 | B SC, S | 19 | Red-brownish | RD6 |
| *amurensis* | B SC, S | 51 | Red | RD1 |

(B—Berry disk, SC—Seed coat, S—Skin)

Example 2

Generation and Characterization of Red Grape Cell Preparations

Materials and Methods

Preparation of AVNIR 825 Cultured Red Grape Cell (RGC) Powder:

The cultured RGC were filtered and thoroughly washed with x2 distilled water, and the wet cells were suspended in water (1:1, v:v) and lyophilized. Alternatively, the washed cells were kept frozen at either −20° C. or −80° C., until further use. The dried RGC powder was ground to a fine powder that was kept at room temperature. Alternatively, the washed cells were ground under liquid nitrogen immediately following washing (or following thawing of the frozen stored cells), and then dried to yield the fine powder.

One gram of ground wet RGC, or 50 mg of lyophilized dried RGC powder, were mixed with 700 μl of M199 medium (Gibco, Cat. No. 22340020) supplemented with 25 μg/ml endothelial mitogen and 5 U heparin, and incubated for 15 minutes at RT with vortexing every 5 minutes. The mixture was centrifuged (20000×g, 15 min, 4° C.) and the supernatant, containing the RGC extract (RGCE) was stored at −20° C. until further use.

Preparation of Wine Samples:

microfuge tubes containing 1 ml of Cabernet Suavignon (Barkan winery, Israel, classic 2003), Petite Sirah (Barkan winery, Israel, classic 2003), Cabernet Suavignon (La Tour de Paris, E.A.R.L. du Domain de Grand Vigne, France 2004) were centrifuged under vacuum in Hetovac V R-1 SpeedVac centrifuge at 40° C. to remove alcohol until a slurry was obtained. Cabernet Suavignon (Byniamina, Israel, 2002) was lyophilized. The tubes were kept at 4° C. or −20° C. until further use. Prior to the bioassay (see below), M199 medium was added so that it resumed its original volume.

Preparation of Grape Seed Extract Samples:

50 mg of dry powder of grape seed extract (GSE) (OPC, batch 40501-0, Whole Health Products, Boulder, Colo., USA) was removed from the capsules and suspended in 300 μl of water, incubated for 15 minutes at room temperature with vortexing every 5 minutes. The mixture was centrifuged (20000×g, 15 min, 4° C.) and the supernatant, containing the solubilized GSE was kept at −20° C. until further use.

Characterization of Grape Extracts:

Polyphenolic compounds were extracted from grounded lyophilized RGC by cold methanol:water:acetic acid (11:5:1). These extracts were subjected to HPLC using an RP-18 column, with (FIG. 1A) or without (FIG. 1B) acid hydrolysis (2N HCl, 60 min., 100° C.), based on the procedure described by Oren-Shamir et al. (Plant Sci., 140:99-106, 1999). Before injecting, the samples were filtrated (Nalgene, 0.45 μm, PVDF). The polyphenol profile was determined using an HPLC (Shimatzu, Japan) equipped with an LC-10AT pump, a SCL-10A controller and a SPD-M10AVP photodiode-array detector. Extract samples were loaded on to the RP-18 column (Vydac 201TP54) and separated by a gradient mixture of the following solutions: DDW (A) and $H_2O$:MeCN:HOAc (107:50:40:3) (B), both solutions at pH 2.3 (titration with $H_3PO_4$ or NaOH). A linear gradient (flow rate of 0.5 ml $min^{-1}$) was applied starting from ratios of 4:1 (A:B) to 3:7 over 45 min, and held at a 3:7 ratio for an additional 10 min. Polyphenol profiles were visualized mainly by their absorbance at 530 nm, 310 nm and 280 nm.

Results

RGC powder was stored at temperatures between −80° C. and Room Temperature (RT) for periods over 18 months with no observable changes. RGC powder was found to be tasteless with no aftertaste as well.

Example 3

Effect of RGC Extract, Red Wine and GSE on ET-1 and eNOS Levels in Human Endothelial Cells The anti-inflammatory power of red grape cell extract of the present invention, Red Wine and GSE was measured by quantitative analysis of their ability to increase the production of eNOS and to inhibit the production of ET-1 in human umbilical vein endothelial cells (HUVEC). As ET-1 is a secreted protein, levels were determined by analyzing the incubation media. eNOS is not a secreted protein and thus eNOS levels were determined in the HUVEC at the end of the incubation period.

Materials and Methods

Preparation of Endothelial Plates:

Human umbilical vein endothelial cells (HUVEC) were supplied from the Hematology Laboratory of Rambam Medical Center as proliferating cells. The flask containing the cells was incubated for one day in a humidified incubator at 37° C. in an atmosphere of 5% $CO_2$. These conditions were maintained throughout the experiment. The cells were then harvested by trypsinization and cryopreserved in identical aliquots. Prior to performing the bioassay, one aliquot was thawed and cultured in a 100 mm dish, precoated with 50 μg/ml fibronectin, containing M199 medium supplemented with 20% FCS, 25 μg/ml endothelial mitogen, 50 μg/ml penicillin, 50 μg/ml streptomycin and 5 U heparin. After the cells reached 70%-90% confluency, they were harvested by trypsinization and were evenly distributed into 24-wells precoated plates. The medium was refreshed every second day.

Incubation of Endothelial Cells with RGC Extract, Red Wine and GSE:

Upon reaching 70%-90% confluency of the cells in the 24-wells plate, samples (300 μl) containing freshly prepared serial dilutions (in a medium devoid of FCS) of either RGC, GSE or Red-wine, were added to the wells and incubated for 6 hours in duplicates. Following incubation, the medium, devoid of the attached cells, was completely collected for ET-1 quantitative determination. The attached cells were washed with PBS and then dissolved in Lammeli solubilization SDS buffer for Western blotting analysis.

ET-1 determination:

The media taken separately from each well was centrifuged, and 50 µl was taken from the supernatant and quantitatively determined for its ET-1 level either by radio-immuno assay (using Endothelin-1 RIA kit No. 5-2024.0001, Bachem AG, Switzerland, results shown in FIG. 1), or by ELISA (Endothelin EIA Kit No. 583151, Cayman Chemical, Ann Harbor Mich., USA, results shown in Table 1). Control of HUVEC incubated in the medium alone were considered as 100% ET-1 production. Assays were performed in duplicates. ET-1 levels in each well were calculated as % of the control.

The threshold concentration of each of the examined RGC Extract, Red Wine and GSE samples, at which ET-1 inhibition was initiated, compared to the control HUVEC, was determined as the lowest inhibitory concentration. The values obtained for ET-1 were normalized relative to the amount of the cells in each well, estimated by the quantitative analysis of the total endogenous tubulin amount in each well (see eNOS determination).

eNOS Determination:

eNOS production was determined by western blot analysis of the solubilized endothelial cells using eNOS specific antibodies (anti NOS3, C20; Santa Cruz Biotechnology, CA, USA). Signal was detected by ECL using peroxidase conjugated second antibody (Amersham) and then visualized on X-ray film or imaged with CCD camera (Alfa Innotech FluoroChem 8800). Determination of the amount of protein in the gel bands was performed by exposing the blot for a second time to anti-β tubulin (H-235 Santa Cruze Biotechnology, CA, USA) followed by the colorimetric detection with alkaline phosphatase second antibody. Quantification of the eNOS bands by spot densitometry (Alfa Innotech software) was normalized relative to the tubulin band intensity.

Cytotoxicity:

As elevated level of red-wine was found to be toxic to the HUVEC, the cells were examined for their cytotoxicity, to eliminate false results, by staining with tetrazolium salt MTT, used as cell viability and proliferating assay, (Corder 2002, Meth. Mol. Biol. 206:147-164). Following collection of the supernatant for ET-1 determination, the cells were washed with M199 medium devoid of phenol red, and incubated for 2 hours with 300 µl of 0.5 mg/ml MTT dissolved in the above medium. Following the incubation, the medium was removed and the insoluble formazan that was produced by the cells was solubilized with 300 µl DMSO and quantified in an ELISA Reader at 570 nm.

Results

Anti-Inflammatory Effect:

Since Cabernet Sauvignon was reported to be among the most potent wines conferring CHD protection (Corder et al, 2001, Nature 414:863-864), it was the primary wine of choice to compare its cardiac-related anti-inflammatory power to that of RGC. Table 3 below summarizes the anti-inflammatory power of RGC preparations, commercial red wines and GSE, as determined by their threshold concentrations that already inhibit the production of ET-1 in vein endothelial cells. The minimal amounts needed for each preparation to initiate inhibition of ET-1 synthesis reflects their potential anti-inflammatory capacity and their potential positive effect in decelerating atherosclerosis.

TABLE 3

| Material | Amount in well |
| --- | --- |
| Cabernet Sauvignon Barkan, classic 2003, IL | 4 µl |
| Syrah Barkan classic 2003, IL | 6 µl |
| Cabernet Sauvignon La Tour de Paris 2004, FR | 3.5 µl; |
| GSE | $>5 \times 10^{-3}$ mg |
| Lyophilized RGC | $1 \times 10^{-3}$ mg |
| Frozen RGC | $7 \times 10^{-3}$ mg (dry weight) |

Figure 2:
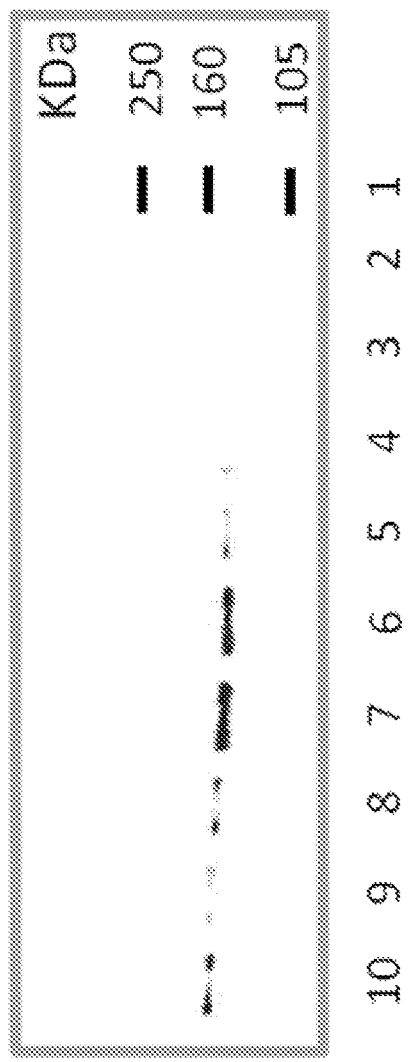
FIG. 2 is a photograph of a Western-Blot analysis of eNOS levels in cultured human endothelial cells, grown on medium in the presence of red grape callus extract. Lanes 2 and 3 illustrate the amount of eNOS in cultured endothelial cells, grown on medium alone. Lanes 4 and 5 illustrate the amount of eNOS in cultured endothelial cells, grown on medium containing an enriched polyphenol fraction obtained from lyophilized Cabernet Sauvignon (Binyamina 2002). Lanes 6 and 7 illustrate the amount of eNOS in cultured endothelial cells, grown on medium containing an extract obtained from 0.25 mg of the red grape callus cells (lane 6) and 0.5 mg of the callus cells (lane 7). Lanes 8 and 9 illustrate the amount of eNOS in cultured endothelial cells, grown on medium containing chicken serum activator taken from feed-restricted (lane 8) and free-fed (lane 9) chickens. Lane 10 illustrates the amount of eNOS in cultured endothelial cells, grown on medium containing commercial Cabernet Sauvignon (Binyamina 2002, IL). Lane 1 is a molecular weight marker.
Figure 3A:
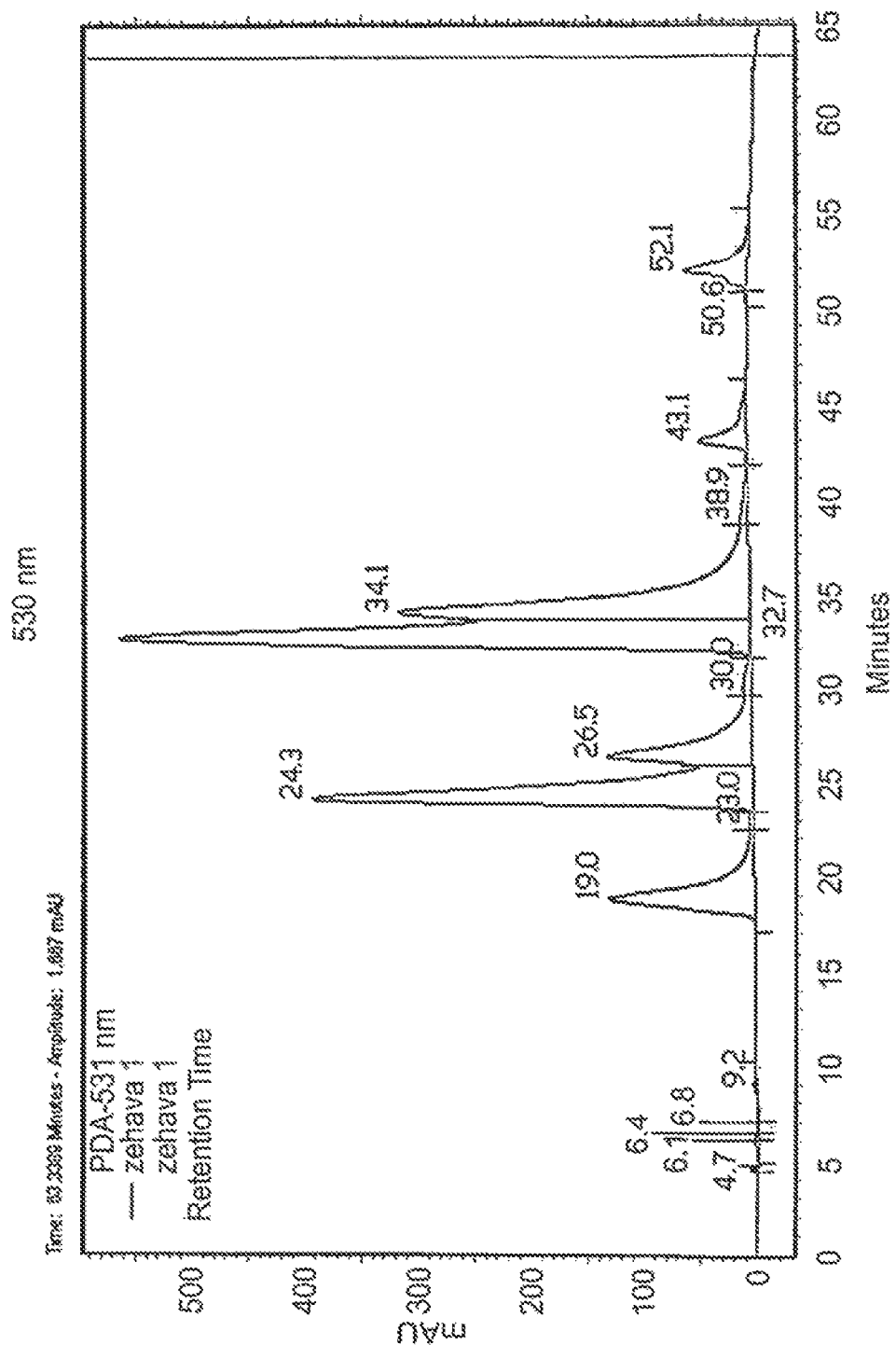
FIGS. 3A-C are HPLC patterns of grape cell line extracts of the present invention following acid hydrolysis (2N HCl, 60 minutes, 100° C.). Polyphenol profiles were visualized by their absorbance at 530 nm (FIG. 3A), 310 nm (FIG. 3B) and 280 nm (FIG. 3C).
Figure 3B:
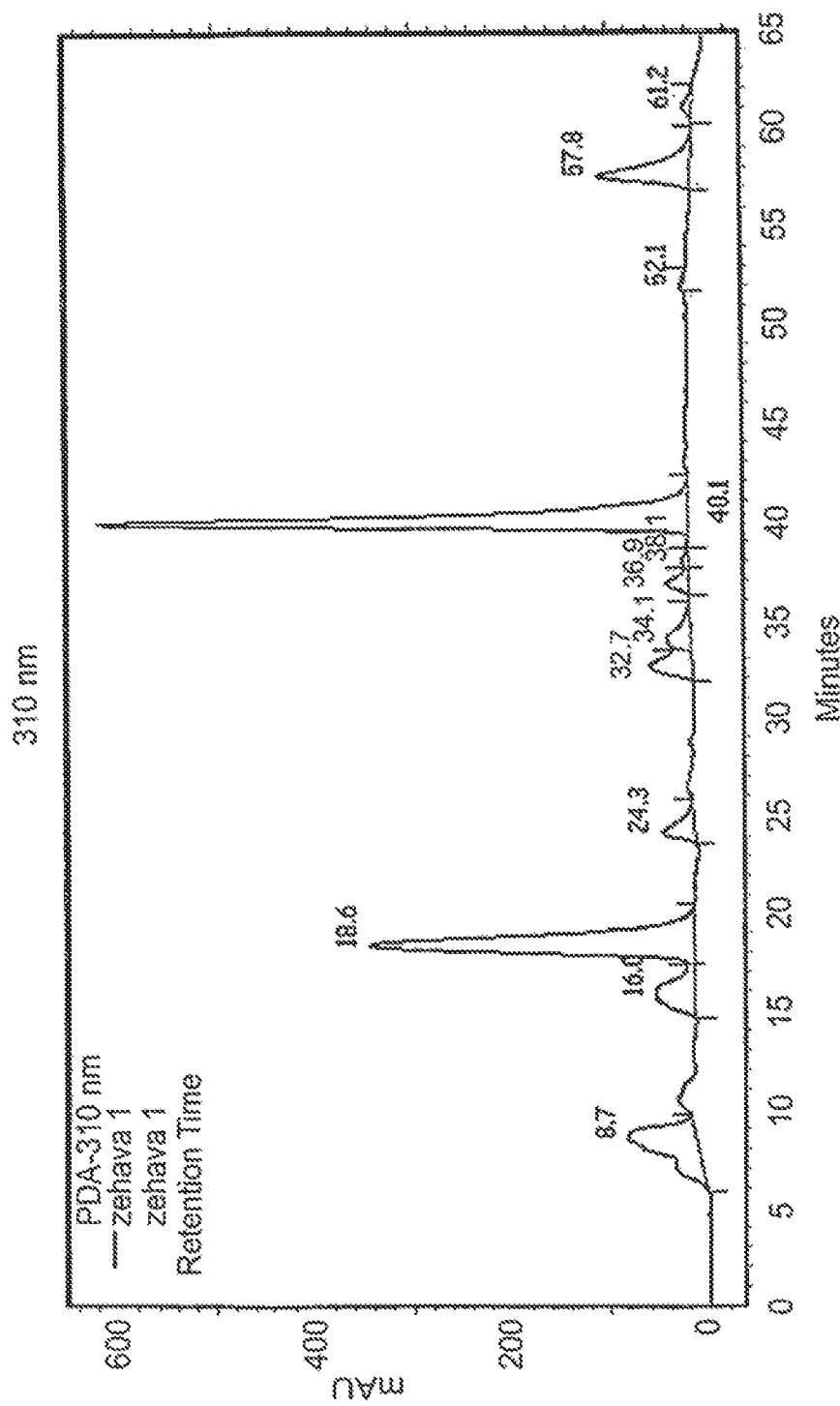
Figure 3C:
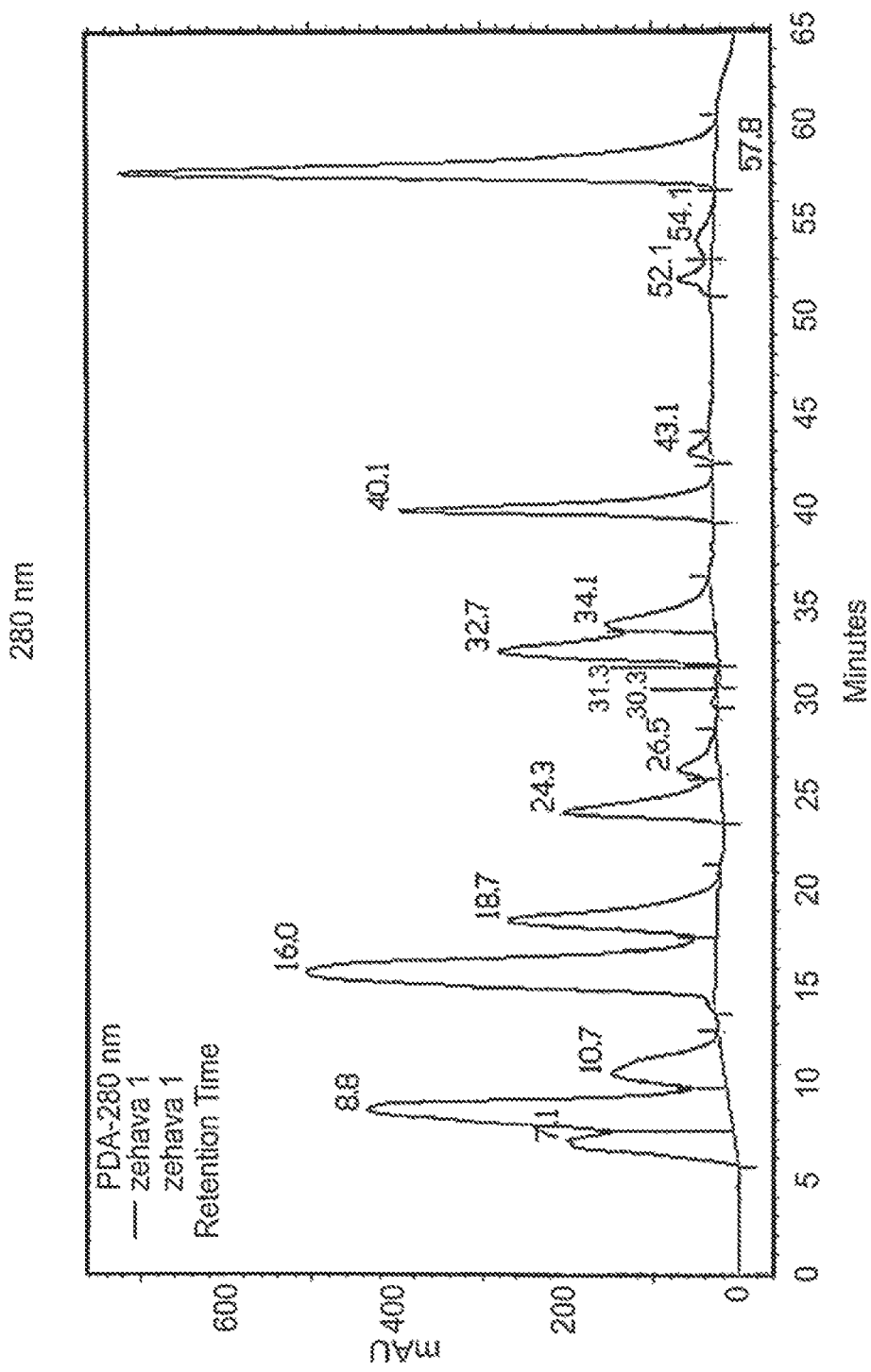
Figure 4A:
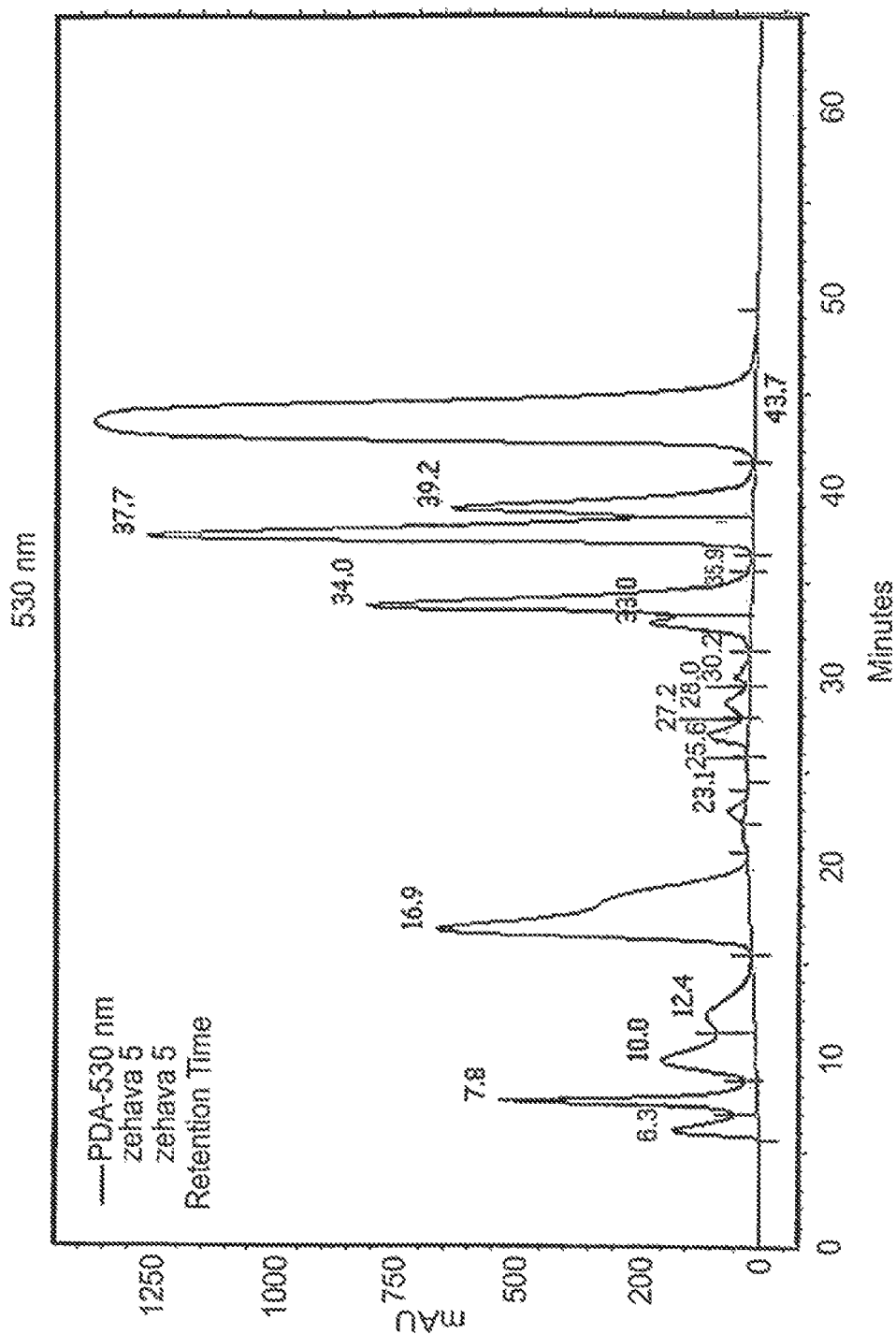
FIGS. 4A-C are HPLC patterns of grape cell line extracts of the present invention without acid hydrolysis. Polyphenol profiles were visualized by their absorbance at 530 nm (FIG. 4A), 310 nm (FIG. 4B) and 280 nm (FIG. 4C).
Figure 4B:
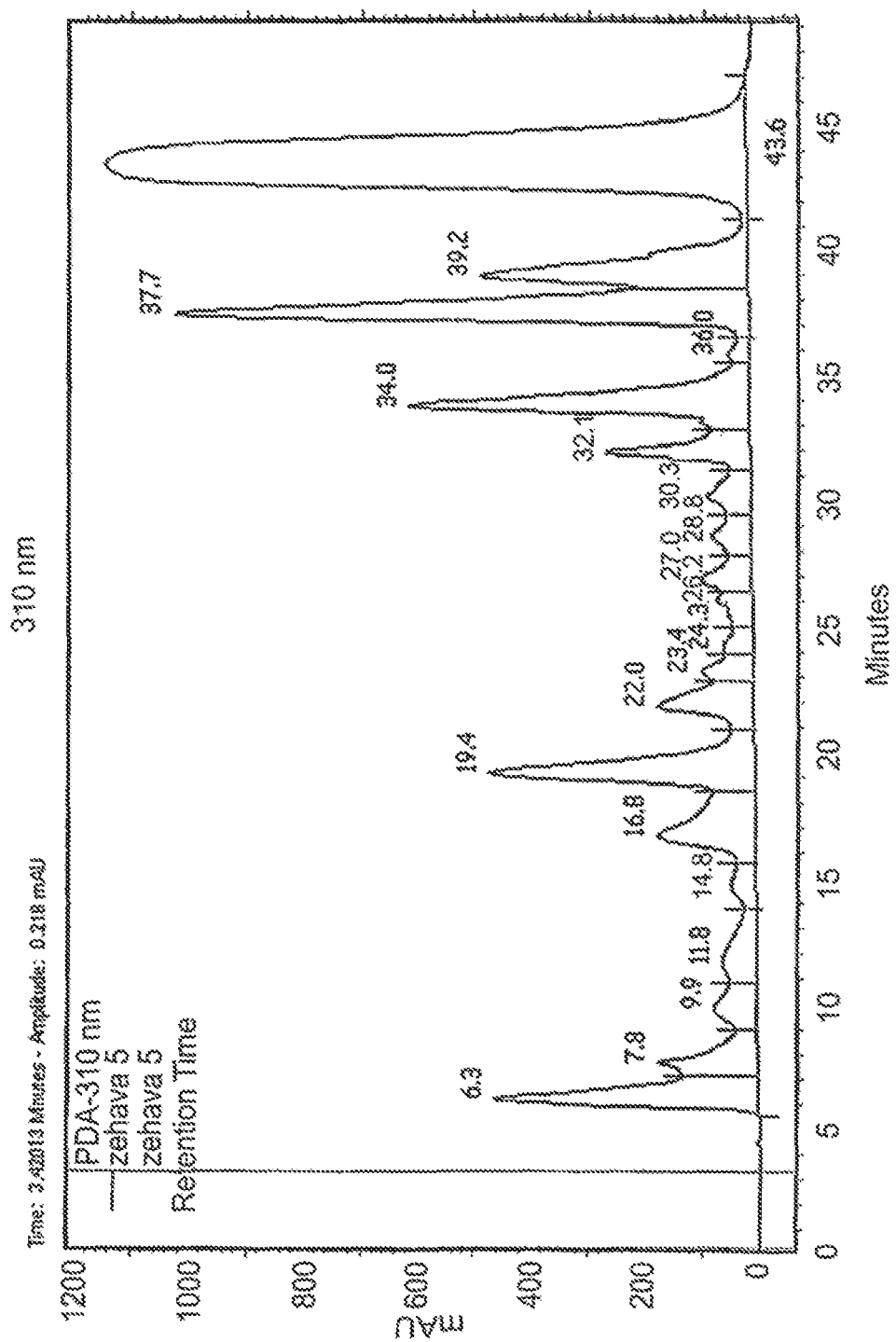
Figure 4C:
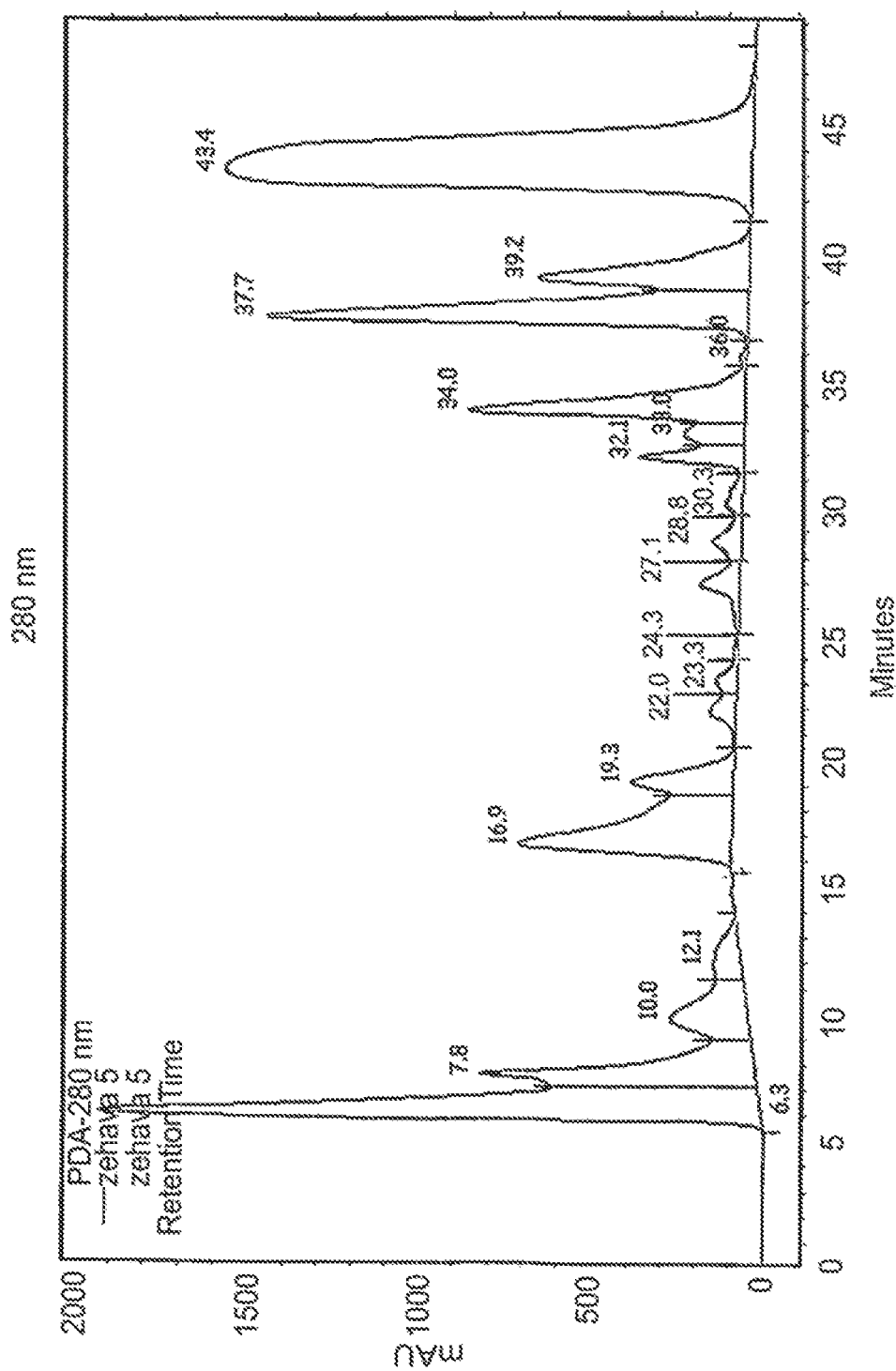

FIG. 1 illustrates the anti-inflammatory effect of RGC, grown on solidified medium, compared to Cabernet Sauvignon (Binyamina 2002, IL). Extract from 16 mg of red grape cells reduced the level of ET-1 ten times greater than 0.12 ml of red wine. Therefore, extract derived from 1 g (fresh wet weight) of grape cells will reduce ET-1 level as efficiently as 75 ml of red wine. As can be seen in FIG. 2, red grape cell extracts activated expression of eNOS to a much greater extent than Cabernet Sauvignon and its polyphenol fractions and 1:2 dilution of serum taken from feed-restricted (lane 8) and free-fed (lane 9) chickens (used as a positive control).

Polyphenol Content:

RGCP contains 3-15% polyphenols (depending mainly on growth conditions and genetic source), compared to 2 g/liter in red wines and over 50% in the commercial GSE tested as determined by the Folin-Ciocalteau micro method (galic acid as standard). Thus, the polyphenol amount needed to completely inhibit ET-1 synthesis in the bioassay is much smaller than that needed in the other products.

Cytotoxicity:

Data obtained from the ET-1 and eNOS bioassays were considered relevant only if cytotoxicity determination performed for each experiment showed that the extract added to the well was not toxic to the HUVEC. Those wells, in which death of HUVE cells was observed, were eliminated from the calculated data. Most of cytotoxicity effects were observed when red wine samples at high concentrations were used.

Example 4

Taste and Aroma Tasting of Grape Cell Extracts of the Present Invention

Under laboratory conditions, 18 calli samples (approx. 2.5-5 g fresh weight) of *Vitis vinifera* cv. AVNIR 825 were collected from growing vessels, washed carefully with running tap water from access growth media, and placed in a 18 multi well plate. The calli were dried by blotting and were further kept at temperatures between 2° C. and 26° C. for 1-5 h. Under these conditions tasting experiments took place by a panel of 10 referees. All 10 referees indicated that all the calli were tasteless and did not indicate any specific unpleasant taste and/or aroma.

In a second experiment performed in an identical fashion, 14 calli samples (approx. 2.5-5 g fresh weight) of *Vitis* species (see Table 2) were tasted by a panel of 10 referees. Nine out of 10 referees, tasting the calli, indicated that the different calli were tasteless and did not indicate any specific unpleasant taste and/or aroma. One referee reported a slight pleasant berry flavor in the *Vitis musdadinia* calli.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A composition consisting essentially of:
a non-extracted, dry cell line callus culture of grape berry cells grown in vitro, whereby the cell line callus culture of grape berry cells is derived from one or more of grape-berry cross section, grape-berry skin, grape-berry flesh, grape seed, grape embryo of seeded or seedless cultivars or grape seed coat;
wherein the composition is a nutraceutical composition.

2. The composition of claim 1, wherein the composition further comprises a nutraceutical acceptable carrier.

3. The composition of claim 1, wherein said cell line callus culture comprises at least 0.5% polyphenols.

4. The composition of claim 3, wherein said cell line callus culture comprises at least 2% polyphenols.

5. The composition of claim 1, wherein said cell line callus culture is derived from a colored or a non-colored grape.

6. The composition of claim 1, wherein said composition is designed for a mucosal delivery.

7. The composition of claim 1, wherein said composition is tasteless.

8. The composition of claim 1, wherein said composition is in a form of mouthwash, a strip, a foam, a powder, a chewing gum, an oral spray, a lozenge, a capsule, a and toothpaste.

9. The composition of claim 1, wherein said composition is in a form of a powder.

10. An alcohol free composition consisting essentially of:
a non-extracted, dry cell line callus culture of grape berry cells grown in vitro, whereby the cell line callus culture of grape berry cells is derived from one or more of grape-berry cross section, grape-berry skin, grape-berry flesh, grape seed, grape embryo of seeded or seedless cultivars or grape seed coat;
wherein the composition is a nutraceutical or a pharmaceutical composition and comprises less than 1% alcohol.

11. A low sugar composition consisting essentially of:
a non-extracted, dry cell line callus culture of grape berry cells grown in vitro, whereby the cell line callus culture of grape berry cells is derived from one or more of grape-berry cross section, grape-berry skin, grape-berry flesh, grape seed, grape embryo of seeded or seedless cultivars or grape seed coat; wherein the composition is a nutraceutical or a pharmaceutical composition and said cell line callus culture of grape berry cells comprises less than 10% sweetening sugar.

12. A composition consisting essentially of:
a non-extracted, dry cell line callus culture of grape berry cells grown in vitro, whereby the cell line callus culture of grape berry cells is derived from one or more of grape-berry cross section, grape-berry skin, grape-berry flesh, grape seed, grape embryo of seeded or seedless cultivars or grape seed coat;
wherein the composition is a pharmaceutical composition.

13. The composition of claim 12, wherein said composition further comprises a pharmaceutically acceptable carrier.

14. The composition of claim 12, wherein said cell line callus culture comprises at least 0.5% polyphenols.

15. The composition of claim 14, wherein said cell line callus culture comprises at least 2% polyphenols.

16. The composition of claim 12, wherein said cell line callus culture is derived from a colored or a non-colored grape.

17. The composition of claim 12, wherein said composition is designed for a mucosal delivery.

18. The composition of claim 12, wherein said composition is tasteless.

19. The composition of claim 12, wherein said composition is in a form of a mouthwash, a strip, a foam, a chewing gum, an oral spray, a lozenge, a capsule, a toothpaste and a food.

20. The composition of claim 19, wherein said composition is in a form of a powder.

* * * * *